(12) United States Patent
Lee

(10) Patent No.: US 10,926,111 B2
(45) Date of Patent: Feb. 23, 2021

(54) BRAGG PEAK DETECTOR USING SCINTILLATORS AND METHOD OF OPERATING THE SAME

(71) Applicant: VIEWORKS CO., LTD., Anyang (KR)

(72) Inventor: Denny Lap Yen Lee, West Chester, PA (US)

(73) Assignee: VIEWORKS CO., LTD., Anyang (KR)

( * ) Notice: Subject to any disclaimer, the term of this patent is extended or adjusted under 35 U.S.C. 154(b) by 0 days.

(21) Appl. No.: 16/824,729

(22) Filed: Mar. 20, 2020

(65) Prior Publication Data

US 2020/0298024 A1    Sep. 24, 2020

Related U.S. Application Data

(60) Provisional application No. 62/821,732, filed on Mar. 21, 2019.

(51) Int. Cl.
*A61N 5/10* (2006.01)
*G01T 1/20* (2006.01)

(52) U.S. Cl.
CPC .......... *A61N 5/1075* (2013.01); *G01T 1/2018* (2013.01)

(58) Field of Classification Search
CPC .............................. A61N 5/1075; G01T 1/2018
See application file for complete search history.

(56) References Cited

U.S. PATENT DOCUMENTS 4,150,292 A * 4/1979 Ter-Pogossian ....... A61B 6/037
250/363.03
4,864,140 A * 9/1989 Rogers .................... G01T 1/172
250/369

(Continued)

FOREIGN PATENT DOCUMENTS

JP    2011-177391 A    9/2011
JP    2017-009393 A    1/2017

(Continued)

OTHER PUBLICATIONS

Ferrero, V. et al., "Online proton therapy monitoring: clinical test of a Silicon-photodetector-based in-beam PET", Sci. Rep. 8, 4100, pp. 1-8 (Year: 2018).*

(Continued)

*Primary Examiner* — Blake C Riddick

(57) ABSTRACT

Provided is a real-time detector of a Bragg peak, comprising: an emitter configured to emit a particle beam toward a target region in a first direction, thereby creating emission of electromagnetic radiation in the target region; a first detection module comprising a stack of first scintillators and first photosensors respectively connected to the first scintillators and configured to detect the electromagnetic radiation and convert into a first signal; a second detection module comprising a stack of second scintillators and second photosensors respectively connected to the second scintillators and configured to detect the electromagnetic radiation and convert into a second signal; and a coincidence detection circuit configured to determine an end point of the particle beam with respect to the first direction based on the first signal and the second signal.

20 Claims, 10 Drawing Sheets

(56) References Cited

U.S. PATENT DOCUMENTS

| | | | |
|---|---|---|---|
| 5,241,181 A * | 8/1993 | Mertens | G01T 1/2985 250/363.03 |
| 6,693,277 B2 | 2/2004 | Cowan et al. | |
| 8,507,842 B2 | 8/2013 | Liang | |
| 8,742,348 B2 | 6/2014 | Nagamine | |
| 9,971,048 B2 | 5/2018 | Shin et al. | |
| 2001/0006215 A1 * | 7/2001 | Cowan | G01N 23/046 250/393 |
| 2003/0062482 A1 * | 4/2003 | Williams | G01T 1/2985 250/363.03 |
| 2003/0105397 A1 * | 6/2003 | Tumer | G01T 1/2985 600/436 |
| 2007/0058778 A1 * | 3/2007 | Coleman | A61N 5/1048 378/65 |
| 2008/0210876 A1 * | 9/2008 | Ishitsu | A61B 6/037 250/363.04 |
| 2009/0080594 A1 * | 3/2009 | Brooks | A61N 5/10 378/4 |
| 2009/0256078 A1 * | 10/2009 | Mazin | A61B 6/54 250/362 |
| 2010/0108896 A1 * | 5/2010 | Surti | G01T 1/00 250/363.04 |
| 2010/0128956 A1 * | 5/2010 | Yamaya | G01T 1/2985 382/132 |
| 2011/0084211 A1 * | 4/2011 | Yamaya | A61N 5/1048 250/363.03 |
| 2011/0092814 A1 * | 4/2011 | Yamaya | A61N 5/1048 600/427 |
| 2011/0147608 A1 * | 6/2011 | Balakin | A61N 5/1049 250/396 R |
| 2012/0150018 A1 * | 6/2012 | Yamaya | G01T 1/2985 600/411 |
| 2012/0165651 A1 * | 6/2012 | Yamaya | A61N 5/1049 600/411 |
| 2012/0253096 A1 * | 10/2012 | Teshigawara | A61N 5/1039 600/1 |
| 2012/0326722 A1 * | 12/2012 | Weinberg | G01R 33/60 324/316 |
| 2013/0023716 A1 * | 1/2013 | Thomas | A61N 5/1071 600/1 |
| 2013/0172658 A1 * | 7/2013 | Brahme | G21G 1/10 600/1 |
| 2013/0190590 A1 * | 7/2013 | Kadir | A61B 6/542 600/407 |
| 2014/0046180 A1 * | 2/2014 | Yamaya | A61B 6/4447 600/427 |
| 2015/0246244 A1 * | 9/2015 | Sossong | A61B 6/4266 600/427 |
| 2015/0297917 A1 * | 10/2015 | Beekman | A61N 5/1067 600/1 |
| 2016/0256713 A1 * | 9/2016 | Saunders | A61N 5/1039 |
| 2016/0300366 A1 * | 10/2016 | El Fakhri | A61B 6/5205 |
| 2016/0338654 A1 * | 11/2016 | Dejongh | A61B 6/4216 |
| 2017/0043183 A1 * | 2/2017 | Balakin | A61N 5/1047 |
| 2017/0112457 A1 * | 4/2017 | Allinson | A61N 5/1077 |
| 2018/0078791 A1 * | 3/2018 | Jung | A61N 5/1084 |
| 2018/0099153 A1 * | 4/2018 | Prieels | A61N 5/1039 |
| 2018/0099154 A1 * | 4/2018 | Prieels | A61N 5/1064 |
| 2018/0250528 A1 | 9/2018 | Liu et al. | |
| 2019/0018154 A1 * | 1/2019 | Olcott | G01T 1/208 |
| 2019/0076673 A1 * | 3/2019 | Lu | A61N 5/1031 |
| 2019/0184197 A1 * | 6/2019 | Fallone | A61N 5/107 |
| 2019/0209867 A1 * | 7/2019 | Sun | G06T 5/002 |
| 2019/0232089 A1 * | 8/2019 | Kleven | A61N 5/1065 |

FOREIGN PATENT DOCUMENTS

| | | | | |
|---|---|---|---|---|
| JP | 2019-154989 A | 9/2019 | | |
| KR | 10-2015-0079242 A | 7/2015 | | |
| WO | WO-2019138384 A1 * | 7/2019 | | G01T 1/2985 |

OTHER PUBLICATIONS

Shakirin, G. et al., "Implementation and workflow for PET monitoring of therapeutic ion irradiation: a comparison of inbeam, in-room, and off-line techniques", Phys. Med. Biol. 56, pp. 1281-1298 (Year: 2011).*

Zhu, X. and El Fakhri, G., "Proton Therapy Verification with PET Imaging", Theranostics 3(10), pp. 731-740 (Year: 2013).*

Bisogni, M.G. et al., "INSIDE in-beam positron emission tomography system for particle range monitoring in hadrontherapy", J. Med. Imag. 4(1), 011005, pp. 1-12 (Year: 2017).*

* cited by examiner

Prior Art

Prior Art

BRAGG PEAK DETECTOR USING SCINTILLATORS AND METHOD OF OPERATING THE SAME

CROSS-REFERENCE TO RELATED APPLICATION

This application claims priority from and the benefit of U.S. Patent Provisional Application No. 62/821,732, filed on Mar. 21, 2019, which is hereby incorporated by reference for all purposes as if fully set forth herein.

BACKGROUND

Field

Exemplary embodiments of the present disclosure relate to a Bragg peak detector and a method of operating the same. Particularly, exemplary embodiments of the present disclosure relate to a real-time in vivo Bragg peak detector for use in particle beam therapy and a method of detecting a Bragg peak in vivo and in real-time during particle beam therapy.

Discussion of the Background

Conventional radiation therapy uses photon energy (e.g., x-ray) to damage or destroy cancerous cells. On the other hand, particle therapy uses charged particles (e.g., protons and heavy ions such as carbon ions). Radiation therapy using particles is of particular benefit in treating cancers that are difficult or dangerous to treat with surgery, and for tumors where conventional radiotherapy would damage surrounding tissue to an unacceptable level.

More specifically, in radiation therapy using particles, a beam of high energy particles is directed to a patient. One advantage of particle therapy in providing treatment is that particles deposit the majority of their ionization dose at a particular location in the body and then travel no further through the body. This effect results in less damage to tissue surrounding a target. However, since the particle beam does not travel through the body, in particle therapy, the particle cannot be detected after passing through the patient, and it has been difficult to accurately detect the energy of the particle beam.

Therefore, there is a need for a method to find out whether a proton beam is radiated to a desired location for treatment and whether the intensity of the proton beam is at a desired level.

Conventionally, the detection or measurement of the proton beam being used to treat the patient has not been possible. Instead, a separate proton beam (test beam) is irradiated against a detector, and the location and intensity of the beam are detected. A separate proton beam (treatment beam) is irradiated against the patient for treatment. However, it is impossible to have real-time detection of the position and intensity of the treatment beam, or "inline dosimetry." Consequently, there may be differences between the position and intensity of the simulated beam and the treatment beam, and treatment effectiveness may be less effective.

Further, during radiation therapy using charged particles, the patient is in a high-background radiation room (i.e., there are significant background x-rays and gamma rays). In such an environment, it is desirable to have a detector that has high detection efficiency for charged particles and low detection efficiency for x-rays or gamma rays.

SUMMARY

Exemplary embodiments of the present invention have been made in an effort to provide an in vivo, real-time Bragg peak detector and a method of detecting a Bragg peak in vivo and in real-time during particle beam therapy.

An exemplary embodiment of the present invention provides a real-time detector of a Bragg peak, comprising: an emitter configured to emit a particle beam toward a target region in a first direction, thereby creating emission of electromagnetic radiation in the target region; a first detection module comprising a stack of first scintillators and first photosensors respectively connected to the first scintillators and configured to detect the electromagnetic radiation and convert into a first signal; a second detection module comprising a stack of second scintillators and second photosensors respectively connected to the second scintillators and configured to detect the electromagnetic radiation and convert into a second signal; and a coincidence detection circuit configured to determine an end point of the particle beam with respect to the first direction based on the first signal and the second signal.

Another exemplary embodiment of the present invention provides a method of detecting a Bragg peak in vivo and in real-time, comprising: emitting a particle beam toward a target region in a first direction, thereby creating emission of electromagnetic radiation in the target region; detecting the electromagnetic radiation and converting into a first signal on a first detection module comprising a stack of first scintillators and first photosensors respectively connected to the first scintillators; detecting the electromagnetic radiation and converting into a second signal on a second detection module comprising a stack of second scintillators and second photosensors respectively connected to the second scintillators; and determining an end point of the particle beam with respect to the first direction based on the first signal and the second signal.

Additional features of the invention will be set forth in the description which follows, and in part will be apparent from the description, or may be learned by practice of the invention.

BRIEF DESCRIPTION OF THE DRAWINGS

The accompanying drawings, which are included to provide a further understanding of the invention and are incorporated in and constitute a part of this specification, illustrate embodiments of the invention, and together with the description serve to explain the principles of the invention.

DETAILED DESCRIPTION OF EXEMPLARY EMBODIMENTS

Figure 1:
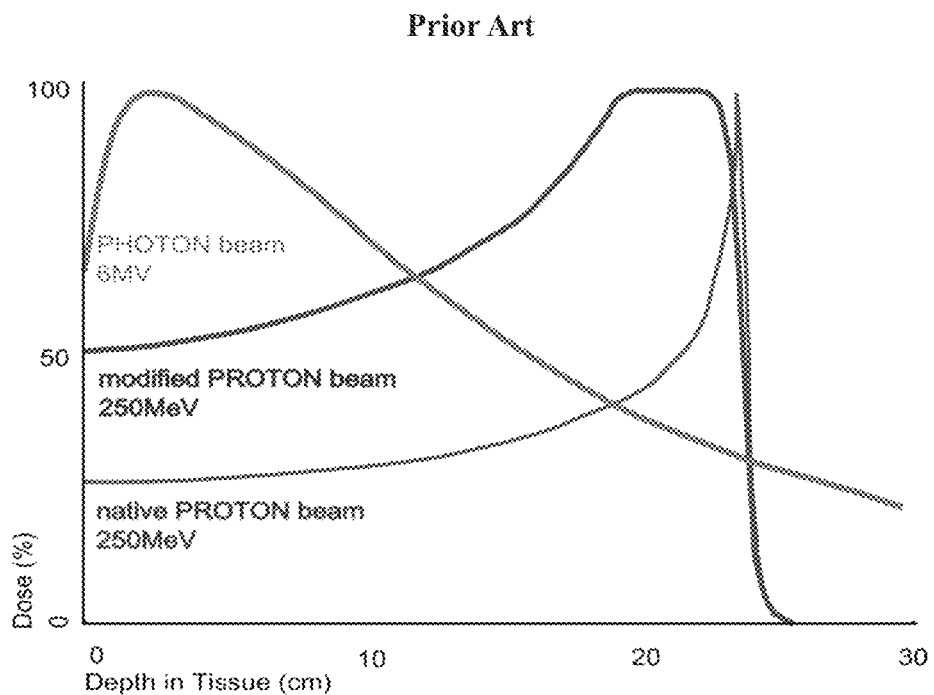
FIG. 1 is a graph showing a comparison of doses delivered by photon and particle beams.

In the following detailed description, only certain exemplary embodiments of the present invention have been shown and described, simply by way of illustration. As those skilled in the art would realize, the described embodiments may be modified in various different ways, all without departing from the spirit or scope of the present invention.

The drawings and description are to be regarded as illustrative in nature and not restrictive. Like reference numerals designate like elements throughout the specification. Further, when the first part is described as being arranged "on" the second part, this indicates that the first part is arranged at an upper side or a lower side of the second part without the limitation to the upper side thereof on the basis of the gravity direction. It will also be understood that when an element or layer is referred to as being "on" or "connected to" another element or layer, it can be directly on or directly connected to the other element or layer, or intervening elements or layers may be present. In contrast, when an element is referred to as being "directly on" or "directly connected to" another element or layer, there are no intervening elements or layers present. It will be understood that for the purposes of this disclosure, "at least one of X, Y, and Z" can be construed as X only, Y only, Z only, or any combination of two or more items X, Y, and Z (e.g., XYZ, XYY, YZ, ZZ).

In the present application, "particles" or "charged particles" may include protons and heavy ions such as carbon ions that can be used in radiation therapy. Although proton therapy may be described as an example in some embodiments of the present invention, it is merely exemplary, and the spirit and scope of the present invention is not limited to proton therapy.

[Human Body (Tissue) Composition and Four Isotopes Generated by High Energy Particle Beam]

When a fast charged particle moves through matter, it ionizes atoms of the material and deposits a radiation dose along its path. The interaction cross section increases as the charge particle's energy decreases. Energy loss by charged particles is inversely proportional to the square of their velocity, which explains the peak occurring just before the particle comes to a complete stop. This phenomenon is exploited in particle therapy of cancer to deliver a high dose to the tumor being treated while minimizing the dose to the surrounding healthy tissue. FIG. 1 shows a comparison of doses delivered by high energy photon beam (gamma rays), to the native proton beam and to the energy modified proton beam.

Human body consists of 65% oxygen, 18% carbon, 10% hydrogen, 3% nitrogen, and 4% other elements, as shown in Table 5 below. When an energetic proton collides with a nucleus, one or multiple nucleons from the nucleus can be separated from the nucleus. These are the (p,n), (p,2n), (p,3n), (p,d), (p,t), (p,a), and etc. nuclear reactions, where p denotes proton, n denotes neutron, d denotes pn (the nucleus of deuteron), t denotes pnn (the nucleus of tritium), and a denotes 2p2n (alpha particle). That is, when an energetic proton (p) is captured by a nucleus of an atom, one or more nucleons can be ejected from the excited nucleus and the atom is transmuted to another isotope of the same element or to an isotope of another element. Since the human body contains a high percentage of oxygen, carbon, nitrogen, and calcium, the collision of energetic proton with the nucleus of these atoms may produce some of their positron emitting isotopes. The major nuclear reactions from oxygen, nitrogen and carbon together with their collision cross-sections are listed in Table 1 below.

TABLE 1

(Average cross-section σ in milli-barns)

| Collision nuclear reaction | Average cross section σ in milli-barns ($10^{-27}$ cm$^2$) | Half life τ of the product isotope in minutes |
|---|---|---|
| $^{16}$O (p, d) $^{15}$O | 70 | 2.04 |
| $^{6}$O (p, α) $^{13}$N | 6.6 | 9.95 |
| $^{6}$O (p, α d) $^{11}$C | 18 | 20.39 |
| $^{6}$O (p, α t) $^{10}$C | 1.85 | 0.32 |
| $^{14}$N (p, d) $^{13}$N | 20 | 9.95 |
| $^{14}$N (p, α) $^{11}$C | 60 | 20.39 |
| $^{14}$N (p, α n) $^{10}$C | 7 | 0.32 |
| $^{12}$C (p, d) $^{11}$C | 90 | 20.39 |
| $^{12}$C (p, d n) $^{10}$C | 4.8 | 0.32 |

Near the end point of the proton beam, four major positron emitting isotopes, $^{15}$O, $^{13}$N, $^{11}$C, and $^{10}$C are produced.

The number N(0) of a certain isotope produced at time zero of proton bombardment by a flux of proton beam Φ is therefore equal to the following expression:

$$N(0) = [\sigma \Phi P(e)] \quad (1)$$

Where σ is the respective collision cross-section of producing that isotope, Φ is the proton flux, and P(e) is the percent abundant of that element in the human body. All the isotopes listed above are unstable and will decay to their daughter isotope with their respective half-life of $\tau_{1/2}$. The number of isotope N(t) remaining at time (t) will therefore be:

$$N(t) = N(0) e^{-(ln2)\frac{t}{\tau_{1/2}}} = N(0) e^{-0.693 \frac{t}{\tau_{1/2}}} \quad (2)$$

The decay rate (that is equal to the positron emission rate) at time (t) is therefore:

$$\frac{dN(t)}{dt} = -\frac{\ln 2}{\tau_{1/2}} N(0) e^{-ln2 \frac{t}{\tau_{1/2}}} = -\frac{0.693}{\tau_{1/2}} N(t) \quad (3)$$

Combining equation (1) with equation (3), the positron emission rate at time (t) from the proton beam is therefore:

$$\frac{dN(t)}{dt} = -\frac{\ln 2}{\tau_{1/2}} N(0) e^{-ln2 \frac{t}{\tau_{1/2}}} = -\frac{0.693}{\tau_{1/2}} [\sigma \Phi P(e)] e^{-ln2 \frac{t}{\tau_{1/2}}} \quad (4)$$

At zero time (t=0) the positron emission rate is therefore:

$$\frac{dN(0)}{dt} = \frac{0.693}{\tau_{1/2}}[\sigma \Phi P(e)] \quad (5)$$

Using equation (4) and equation (5), and also using the percent abundance of elements in human body as 65% oxygen, 18% carbon, and 3% nitrogen, positron isotopes generation rates and positron isotopes activity are obtained as follows:

TABLE 2

(Positron isotopes generation rate at t = 0 and t = 10)

| Element in human body P(e) | Proton activation | Average collision cross-section σ O⁻²⁷ cm² | Half life of product isotope τ in minutes | Positron emission rate at t = 0 Per unit flux Φ | Positron emission rate at t = 10 min. Per unit flux Φ |
|---|---|---|---|---|---|
| Oxygen 65% | ¹⁶O(p, d)¹⁵O | 70 | 2.04 | 15.46 | 0.5174 |
| Oxygen 65% | ⁶O(p, α)¹³N | 6.6 | 9.95 | 0.3 | 0.15 |
| Oxygen 65% | ⁶O(p, αd)¹¹C | 18 | 20.39 | 0.398 | 0.283 |
| Oxygen 65% | ⁶O(p, αt)¹⁰C | 1.85 | 0.32 | 2.60 | 0 |
| Nitrogen 3% | ¹⁴N(p, d)¹³N | 20 | 9.95 | 0.04 | 0.02 |
| Nitrogen 3% | ¹⁴N(p, α)¹¹C | 60 | 20.39 | 0.061 | 0.043 |
| Nitrogen 3% | ¹⁴N(p, αn)¹⁰C | 7 | 0.32 | 0.455 | 0 |
| Carbon 18% | ¹²C(p, d)¹¹C | 90 | 20.39 | 0.55 | 0.392 |
| Carbon 18% | ¹²C(p, dn)¹⁰C | 4.8 | 0.32 | 1.8711 | 0 |

TABLE 3

(Weighted positron isotopes generation rate of ¹⁵O, ¹³N, ¹¹C, and ¹⁰C by proton beam at t = 0, and the relative positron activity in time)

| β⁺ emitter isotope | Weighted collision cross-section | Half Life | Combined positron emission rate at t = 0 per unit flux Φ | Combined positron emission rate at t = 10 min. per unit flux Φ | Combined positron emission rate at time τ Per unit flux Φ |
|---|---|---|---|---|---|
| ¹⁵O | 45.5 | 2.04 | 15.46 | 0.5174 | 15.46e⁻⁰·⁶⁹³ᵗ/²·⁰⁴ |
| ¹³N | 4.89 | 9.95 | 0.34 | 0.17 | 0.34e⁻⁰·⁶⁹³ᵗ/⁹·⁹⁵ |
| ¹¹C | 29.7 | 20.39 | 1.01 | 0.718 | 1.01e⁻⁰·⁶⁹³ᵗ/²⁰·³⁹ |
| ¹⁰C | 2.27 | 0.32 | 4.926 | 0 | 4.926e⁻⁰·⁶⁹³ᵗ/⁰·³² |

Figure 2:
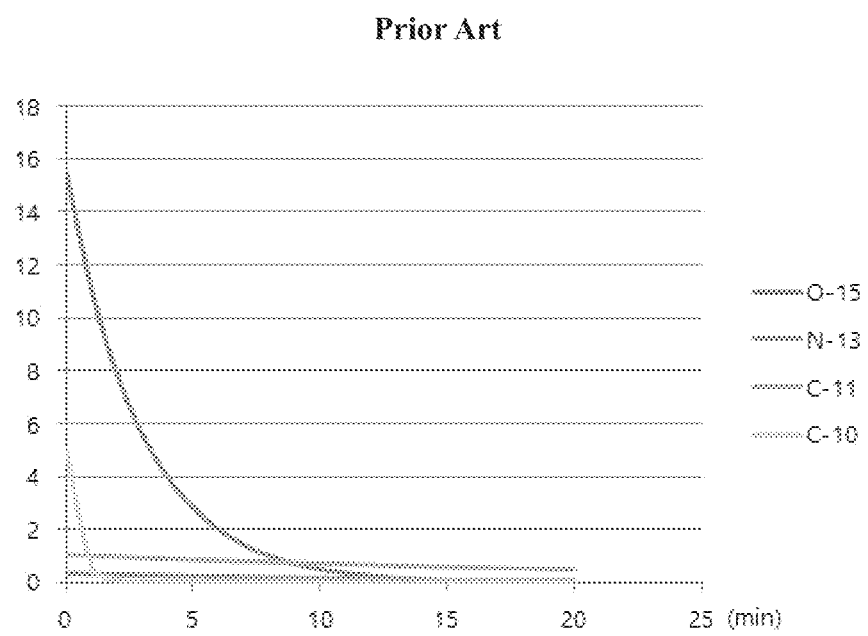
FIG. 2 is a graph showing positron generation from transmuted isotopes.

FIG. 2 shows positron generation from ¹⁵O, ¹³N, ¹¹C, and ¹⁰C from t=0 to t=20 minutes. The total sum of positron isotopes activity at t=0 and t=10 is obtained by summing from the above tables, which is shown in Table 4 below.

TABLE 4

(Total sum of positron isotopes activity at t = 0 and t = 10)

| Elements total in human body | β⁺ emitter isotopes | Total average collision cross-section σ 10⁻²⁷ cm² | Sum of Positron emission rate at t = 0 | Sum of Positron emission rate at t = 10 min. |
|---|---|---|---|---|
| 86% | ¹⁵O, ¹³N, ¹¹C, ¹⁰C | 82.36 | 21.7 | 1.4 |

TABLE 5

(Elements in human body)

| Element | Carbon | Oxygen | Hydrogen | Nitrogen | Calcium | Phosphorus | Other |
|---|---|---|---|---|---|---|---|
| Percentage (%, mass) | 18 | 65 | 10 | 3 | 1.5 | 1 | 1.5 |

[In Vivo Bragg Peak Detection Using Back-to-Back Gammas Generated by Particle Beam]

Figure 3:
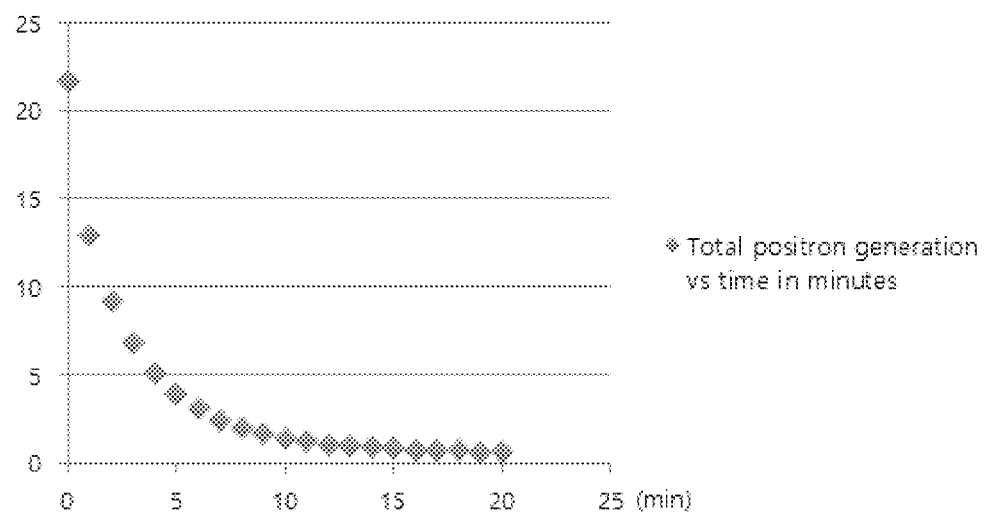
FIG. 3 is a graph showing total positron generation from proton beam verses time.

FIG. 3 shows total positron generation from proton beam verses time in minutes. T=0 is real time at which the proton beam is turned on. Referring to FIG. 3, it can be found that most of the positrons are generated in the first 4 minutes and the instantaneous rate is the highest at t=0, or when the proton beam is on. This also means that the positron density is the highest at real time (t=0) and is concentrated at the end point of the proton beam.

Positron is an anti-particle. When this low energy positron encounters an electron from the nearby tissue (mostly within 2 mm), it will be annihilated by the following reaction:

Positron+Electron→2 gammas(511 KeV each)

The conservation law of energy and momentum requires the direction of these two gamma radiation to be 180 degrees apart (emitting simultaneously in opposite directions, or it is called back-to-back gammas). Using conventional two position sensitive gamma ray detectors such as Positron Emission Tomography (PET) detectors, these two back-to-back gammas can be traced. Knowing the travel time of light, the time differences of the detection of these two back-to-back gammas can roughly determine the position of the emitting isotope along this line. However, the accuracy of position using the travel time differences is much less than the accuracy of the line itself. Therefore, by using conventional detectors alone, additional information is needed to determine the end point of the therapeutic proton beam. Also, conventional detectors which are designed to locate positron emitting isotopes are not ideal for locating the therapeutic proton beam in real time because of the following reasons:

(1) Two dimensional position sensitive gamma ray detectors designed for conventional PET can only function well in a relatively radiation "quiet" environment. During proton therapy, high intensity of "prompt" gamma rays are also emitting along the track of the particle beam. This high radiation background of prompt gamma rays in the treatment room when the therapeutic beam is on could also be detected by the conventional PET detectors and could produce a high degree of "pile up" or ambiguity in the determination of the true back-to-back 511 KeV gammas of interest. Since the half-lives of isotope $^{11}$C and $^{13}$N produced in human body during particle therapy are in the order of 10 to 20 minutes, conventional PET detectors can be used soon after the treatment for verification by moving the patient to a radiation "quiet" environment. However, it was found that because of the diffusion of body fluids (wash out effect) and the displacement of body parts, after the real time treatment, the accuracy of the "off time" position determination is not sufficiently accurate for treatment verification. A "real time" Bragg Peak detector is therefore very desirable.

(2) Commercially available conventional PET detectors designed for tomography are both bulky and expensive and are very difficult to integrate into the proton beam treatment room.

(3) Conventional PET detectors using solid state detectors are susceptible to radiation damage in the high radiation environment of the particle therapy treatment room. Radiation hard detectors such as photomultiplier tubes (PMT) or radiation hard solid state detectors may be beneficial for this application.

Referring to FIG. 3 and Table 4, it is found that at the time when the proton beam is on (during the proton therapy), the emission rate of positron at t=0 is 15 times higher than 10 minutes later when the patient is moved to a PET room for treatment verification. Therefore, it will be more precise to detect the Bragg peak of the particle beam in real time during a particle therapy.

[In Vivo, Real-Time Bragg Peak Detector]

Figure 4:
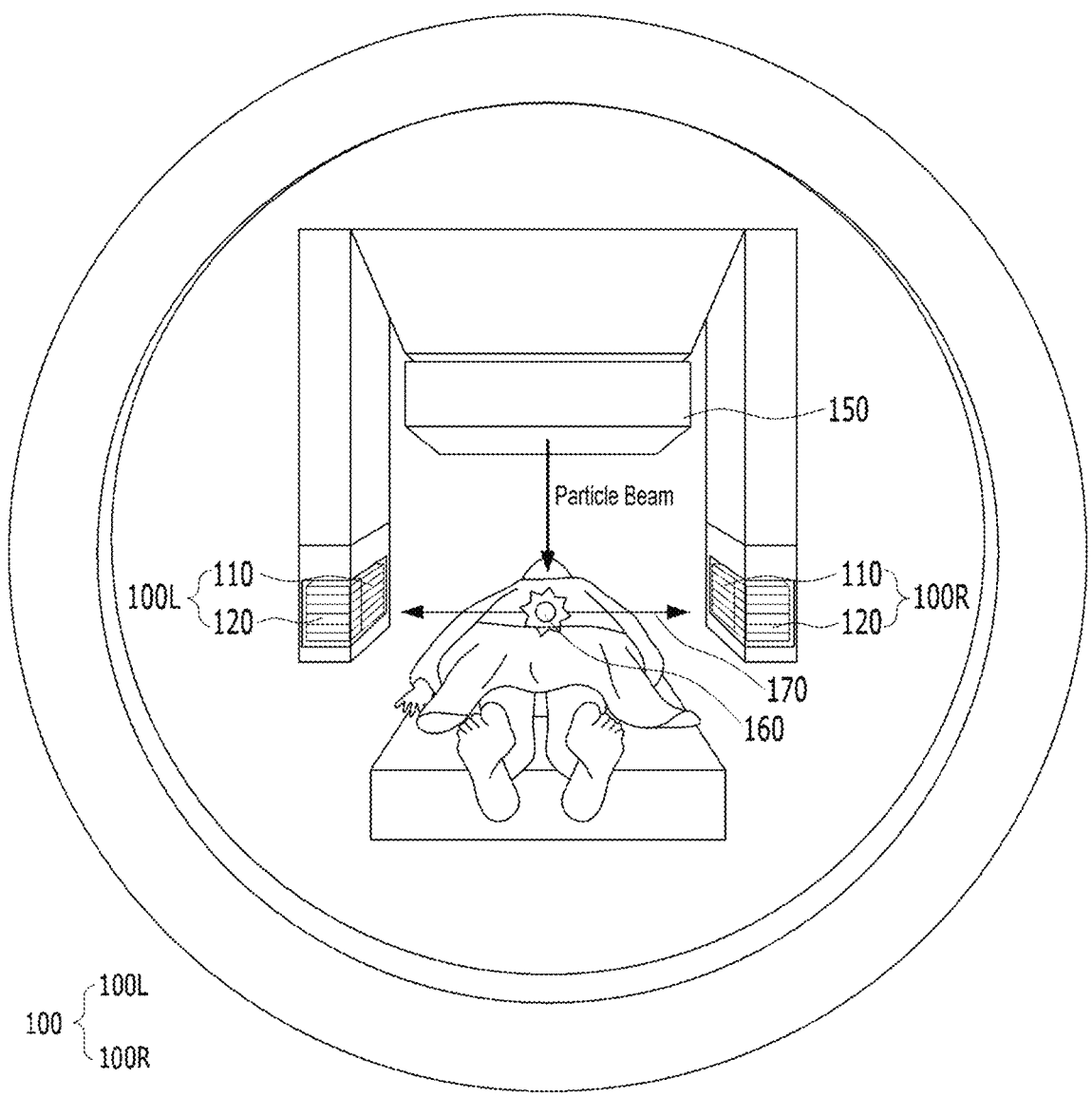
FIG. 4 is a schematic view of a detector in a particle beam treatment room in accordance with one exemplary embodiment of the present disclosure.

FIG. 4 is a schematic view of a detector in a particle beam treatment room in accordance with one exemplary embodiment of the present disclosure.

Referring to FIG. 4, the emitter 150 is provided to emit a beam of charged particles such as protons or heavy ions (e.g., carbon ions) to the target point (or target region) 160 of a patient or a test subject. When the charged particles collide with matter in the patient or test subject, positrons are generated and subsequently annihilate upon encounter with nearby electrons to generate the back-to-back gammas 170. Gamma-rays are a form of electromagnetic radiation, and the annihilation of a positron and an electron creates emission of electromagnetic radiation (e.g., two gammas) in opposite directions.

In accordance with one exemplary embodiment of the present disclosure, the z-detection module 100 is provided to detect the back-to-back gammas 170 and measure the position of the end point (i.e., the Bragg peak) of the particle beam. One z-detection module 100 includes a stack of scintillators 110 and photosensors 120.

In order to detect gammas in opposite directions, a pair of z-detection modules 100 are provided on both sides of the target region 160. In one embodiment, the pair of z-detection modules 100 (i.e., left z-detection module 100L and right z-detection module 100R) are disposed to face each other on opposite sides across the target region 160.

In accordance with one exemplary embodiment, each of the pair of z-detector modules 100 may include a scintillator stack 110 and a photosensor stack 120. The scintillator stack 110 may include a stack of n scintillators 110-1~110-$n$ that are stacked on top of each other, and the photosensor stack 120 may include a stack of n photosensors 120-1~120-$n$ that are stacked on top of each other. In one exemplary embodiment, one scintillator 110-$n$ and one photosensor 120-$n$ may be connected to form a basic detection element. Further, a pair of basic detection elements aligned in coplanarity (i.e., one basic detection element in the left detection module 110L and another basic detection element in the right detection module 110R aligned in the same z-plane) may form a basic detection unit.

Figure 5A:
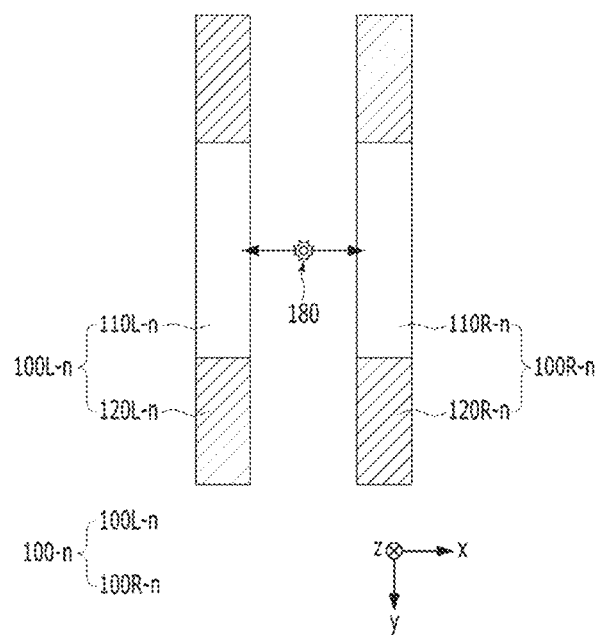
FIG. 5A is a top view of a basic detection unit.
Figure 5B:
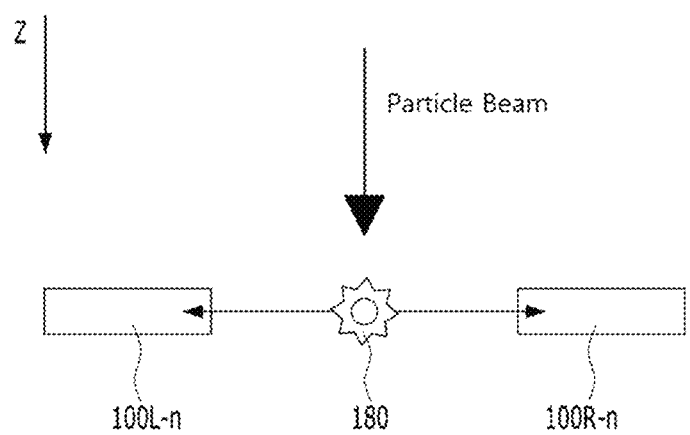
FIG. 5B is a front view of the basic detection unit in accordance with one exemplary embodiment of the present disclosure.

FIG. 5A is a top view of a basic detection unit, and FIG. 5B is a front view of the basic detection unit in accordance with one exemplary embodiment of the present disclosure.

Referring to FIGS. 5A and 5B, a coplanar arrangement of one basic detection unit 100-$n$ among the z-detection modules 100 is selected and presented. One particular detection unit 100-$n$ among the z-detector modules 100 may determine the plane of interest, i.e., the plane containing the travels by the back-to-back gammas originated from the particle end point 180 and perpendicular to the particle beam. A stack of n basic detection units 100-$n$ (n can be 1 to any suitable number depending on the range in z-direction that back-to-back gammas may reach and the thickness of each scintillator, e.g., 100, 120, 150, etc.) aligned in coplanarity may form the z-detector modules 100. The plane of each detection unit 100-$n$ may be perpendicular to the direction of the particle beam.

In one embodiment, multiple detection elements, each including a sheet, plate, a strip, or other flat-shaped scintillator connected to a photosensor are stacked on top of each other in the thickness dimension of the scintillator and the photo sensor, such that the stacked thicknesses of the separate detection elements define the height of the stacked detection module, where the height dimension is perpendicular to the plane defined by the length and width of each of the stacked scintillator and photosensors.

In accordance with one exemplary embodiment of the invention, the detection elements, each including the scintillator 110-$n$ connected to the photosensor 120-$n$, may be arranged relative to the emitter 150, such that when the target point or region 160 is arranged to be coplanar with one sheet of scintillator 110-$n$ (or the plane defined by the length and width of one sheet of scintillator 110-$n$), back-to-back gammas from the annihilation of positron generated at the end point 180 as a result of interaction of the particle beam with a substance at the end point 180 can be detected by one pair of detection elements (i.e., one basic detection unit 100-$n$) arranged on the same plane as that of the end point 180 and the travel path of the back-to-back gammas. In one embodiment, the emitter 150 may be a proton beam or a heavy ion beam. Further, the target point (or region) 160 may be a position defining the end point 180 of a nuclear reaction of the charged particle of the particle beam, at which a positron isotope is generated in a material at the target region 160.

In accordance with one exemplary embodiment, the scintillator 110-$n$ may include a sheet, a strip, or a plate of scintillation material such as NE102, PILOT U, BC418, YSO or LYSO. The scintillator 110-$n$ may include any suitable scintillation material in the pertinent art. For example, short lag time and fast response scintillators like plastic scintillation materials may be used. Because a short coincident time window is effective in rejecting most of the accidental detection (e.g., pile-up problem and others) from prompt x-ray, scintillation materials with short decay time (e.g., 0.01 ns~1,000 ns) may be used in one embodiment. Exemplary scintillation materials include, but not limited to plastic scintillators (e.g., NE102, BC418, etc.), LYSO, YSO, BGO($Bi_4Ge_3O_{12}$), and NaI.

Depending on the x-ray absorption coefficient of the scintillation material, the width of the scintillator 110-$n$ in the x-direction may be determined such that it is sufficient to absorb a major portion of the 511 KeV gammas traversing through. For example, the width of the scintillator 110-$n$ may be 5 cm or more for plastic scintillators or 2 cm or more for YSO or LYSO. Further, the shape of the scintillator 110-*n* may vary depending on the number of photosensors connected thereto (e.g., polygons as shown in FIG. 6B).

In accordance with one embodiment, the scintillator 110-*n* may be connected at one end (or at two ends) to the photosensor 120-*n*, which may be a photomultiplier tube (PMT) or a solid state detector, for instance. In one embodiment, the scintillator 110-*n* may be a sheet shape or a substantially thin and flat shape in a thickness dimension, while being longer in length and width dimensions. The scintillator material may absorb one of the back-to-back gammas from the annihilation of the positron produced by the isotopes at the end point 180 of a particle beam. For example, the photosensor 120-*n* may be a PMT together with light pipes or light guiding elements coupled to the scintillator 110-*n* for the detection of the scintillation light from the scintillator 110-*n*. The length and thickness dimensions of the scintillator 110-*n* of each pair of detection elements may be coplanar to each other. The thickness dimension of the scintillator 110-*n* (e.g., z-direction) is perpendicular to the plane defined by the length and width of the scintillator 110-*n* (e.g., x-y plane).

In accordance with one exemplary embodiment, the photosensor 120-*n* connected to the scintillator 110-*n* is capable of detecting the back-to-back gammas from the annihilation of the positron at the end point 180 of the particle beam and generates an electrical signal based on detecting the scintillation lights. The photosensor 120-*n* may be, for example, a photomultiplier tube (PMT) or a radiation hard solid state detector with fast response time (e.g., sub-nanosecond to microsecond). In order to minimize the accidental rate (i.e., false signal from background radiation), the output pulse from the photosensor 120-*n* may be as short as possible (e.g., 1.4 nano-seconds, using PILOT U or BC418).

Figure 6A:
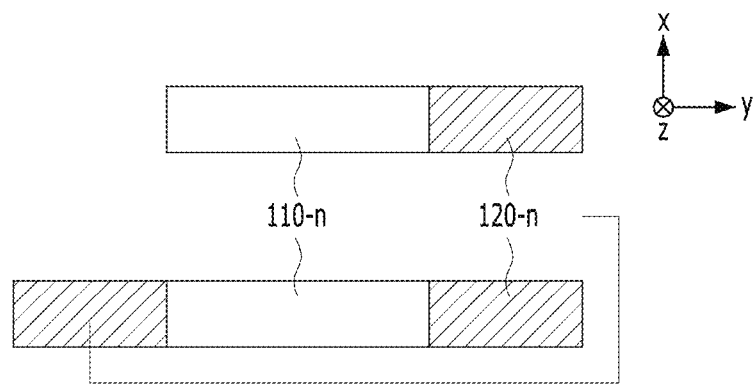
FIGS. 6A and 6B are top views of basic units in accordance with another embodiment of the present disclosure.
Figure 6B:
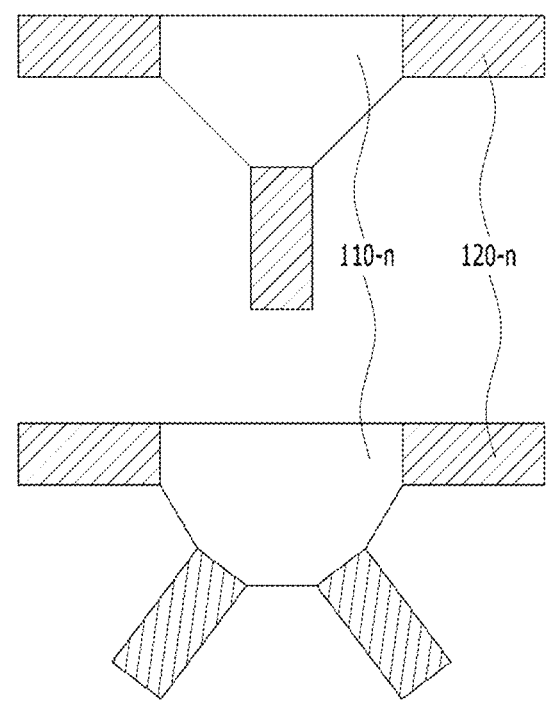

FIGS. 6A and 6B are top views of basic detection units in accordance with other embodiments of the present disclosure. Referring to FIG. 6A, one photosensor 120-*n* with one sheet of scintillator 110-*n* may form one detection element. Alternatively, using two photosensors 120-*n* with one sheet of scintillator 110-*n* is also possible.

Referring to FIG. 6B, one scintillator 110-*n* with three or more photosensors 120-*n* may form one detection element. Those skilled in the art will appreciate that any suitable number of photosensors 120-*n* may be connected with one scintillator to properly detect back-to-back gammas. Further, as shown in FIGS. 6A and 6B, the shape and dimensions of the scintillator 110-*n* may vary depending on the number of photosensors connected thereto and the type of scintillation material.

Figure 7A:
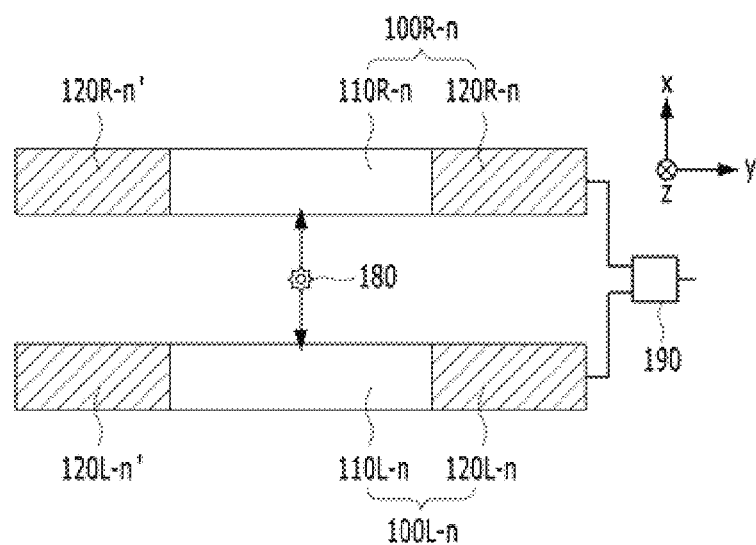
FIG. 7A is a schematic diagram of a detector.
Figure 7B:
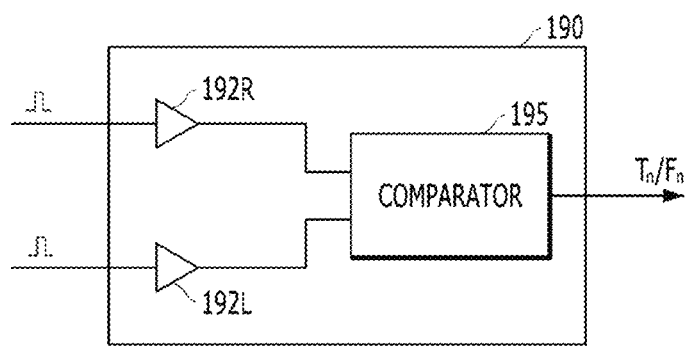
FIG. 7B is an exemplary configuration of the coincidence detection circuit in accordance with one exemplary embodiment of the present disclosure.

FIG. 7A is a schematic diagram of a detector, and FIG. 7B is an exemplary configuration of the coincidence detection circuit in accordance with one exemplary embodiment of the present disclosure.

In accordance with one exemplary embodiment, the coincidence detection circuit 190 may be connected to the photosensors 120L-n and 120R-n to determine a true event of detecting the z-position of the back-to-back gammas.

When a pair of back-to-back gammas produce scintillation lights in both detection elements 100L-n and 100R-n, short signal pulses will be produced by both photosensors 120L-n and 120R-n within the decay time of the scintillation material or the time constant of the photosensors, whichever is longer. This pair of simultaneous pulses from the photosensors 120L-n and 120R-n will signify a true event of back-to-back gamma along the z-plane where the pair of detection elements 100L-n and 100R-n are located.

Other background radiation may also produce scintillation lights and therefore photosensor output pulses. However, background radiation unrelated to the annihilation of positron at that particular z-plane will be random in time, and the chance of producing a false event signal is inversely proportional to the time window used in the coincidence detection circuit and the solid angle of the detection elements. For example, if the time window may be set at a few nano-seconds, e.g., 2 ns, the occurrence of a false event from random background radiation will be insignificant if the background rate is less than 1E7 per second.

Referring to FIG. 7B, the coincidence detection circuit 190 may be a digital logic circuit including the first amplifier 192L to amplify the pulse from one photosensor 120L-n, the second amplifier 192R to amplify the pulse from the other photosensor 120R-n, and a comparator 195 to compare the amplified pulses from the amplifiers 192L, 192R to determine whether the two pulses are within a certain time window (e.g., 2 ns, 2.5 ns, etc.). The comparator 195 may output a True signal (e.g., logic high) in response to determining that the two pulses are within the time window, whereas outputting a False signal (e.g., logic low) in response to determining that the two pulses are outside the time window. The comparator 195 may be adjusted to have a variable time window. In one embodiment, the amplifiers 192L, 192R may be omitted. Further, computing circuitry (not shown) may be connected to the coincidence detection circuit 190 and configured to identify, in the case of a True signal, the z-position of the particular scintillator 110-*n*, which detected the back-to-back gammas, as that of the end point. The coincidence detection circuit 190 may be provided for each detection unit separately or for multiple detection units collectively. Even if the coincidence detection circuit 190 would be provided for each detection unit separately, all or part of the constituting circuit elements may be integrated into one circuit board or a single semiconductor chip. In addition, the coincidence detection circuit 190 and the comparator 195 may include hardware circuitry, with software/firmware installed thereon, capable of performing logic and/or arithmetic operations.

Referring back to FIG. 7A, additional photosensors (e.g., 120L-n' and 120R-n') may be connected with one scintillator 110L-n or 110R-n. That is, there may be two or more photosensors connected to each scintillator 110L-n and 110R-n for a total of four or more photosensors. Although not shown, all the photosensors (e.g., 120L-n, 120L-n', 120R-n, and 120R-n' in the example shown in FIG. 7A) may be connected to the coincidence detection circuit 190. In one embodiment, outputs from the photosensors 120L-n, 120L-n' may be ORed with each other, while outputs from the photosensors 120R-n, 120R-n' may be ORed with each other, before respective OR results are compared for coincidence in the coincidence detection circuit 190. In other words, regardless of the number of photosensors connected to one scintillator, outputs from photosensors connected to the same scintillator may be subject to an OR logic operation prior to being compared with an OR result of outputs from the counterpart scintillator.

The efficiency of detection for a positron-electron annihilation event at the respective z-position is also proportional to the solid angle sustained by the length of the scintillator 110-*n* (y-direction) and the thickness in the z-direction. The accuracy of the z-direction is proportional to the thickness in the z-direction.

For a "coincident" time window of a few nano-seconds (e.g., 2 ns), the "accidental" detection of a prompt gamma within this time window will be insignificant unless the flux of the prompt gammas falling within the solid angle of the detector element is higher than 5E8 per second. By way of example, for plastic scintillation material (e.g. BC418 from Saint Gobain Crystal of USA) of 50 cm long by 3.5 cm wide and a thickness of 2 mm (along the z-plane), and if it is placed 25 cm from the proton beam, it will sustain a solid angle of 3.18E-4 for each pair of detection elements. When each pair of detection element is operating in the "coincident detection mode" of a time window of about 2 nano-seconds, the prompt gammas production rate when the proton beam is "on" will need to be higher than 6E11 per second (or 100 nA) before excessive "accidental" coincident or "signal pulses pile up" is significant. For a typical proton therapy beam in the order of 10 nA, the prompt gamma accidental rate will be insignificant using this small solid angle and short coincident time window. A short coincident time window is therefore effective in rejecting most of the accidental detection from prompt gammas, or x-rays. Using such a short time window, back-to-back gammas from the position annihilation can therefore be detected during particle therapy, in real time and in vivo. For the proton beam current of 10 nA, a time window of 100 ns or less can maintain a relatively clean detection of the back-to-back gammas in real time and in vivo without excessive signal pulse "pile up." Using a pair of PET detector in a similar geometry, the solid angle of a 30 cm×30 cm PET detector head at a distance of 25 cm from the beam will have a solid angle of about 0.11. The coincident rate from the prompt gammas from a proton beam of 0.3 nA will produce excessive "accidental" event or pulses pile up to make the detection of true back-to-back gammas of 511 KeV impossible. From this example, it can be found that a small solid angle from each detection element and a short coincident time window are both enabling factors for the detection of the short half life positron emitting isotopes in real time and in vivo.

Figure 8:
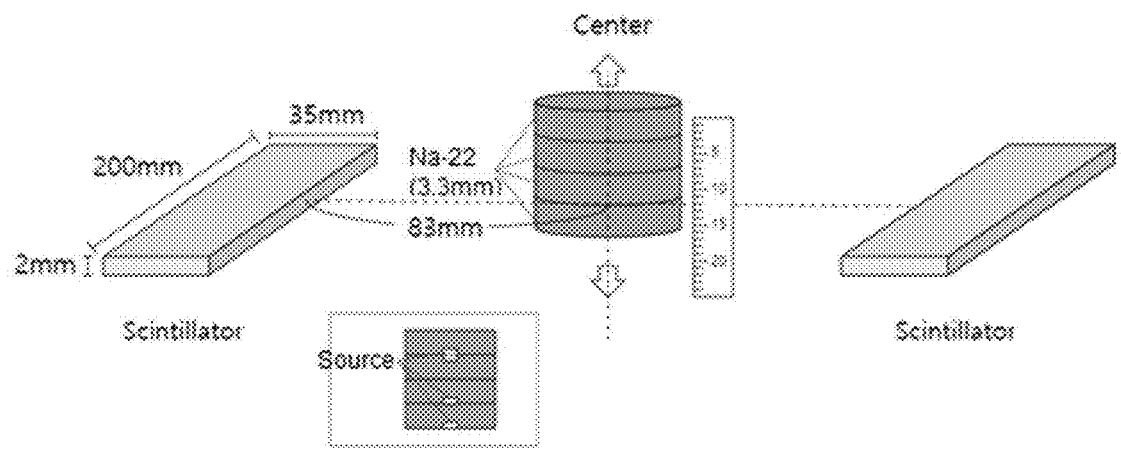
FIG. 8 shows the geometry of test sources using Na-22 positron isotope.
Figure 9:
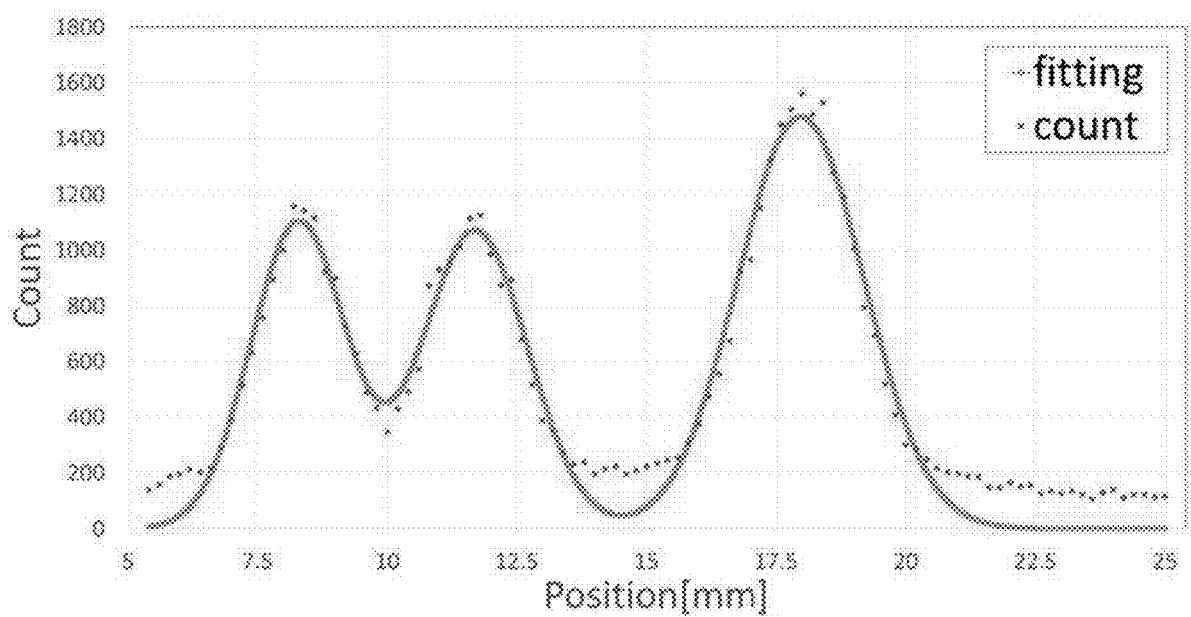
FIG. 9 is a graph of signals detected by a pair of z-detector units having a resolution of 2 mm.

FIG. 8 shows the geometry of test sources using Na-22 positron isotope, and FIG. 9 is a graph of signals detected by a pair of z-detector units having a resolution of 2 mm. Referring to FIG. 8, sources of Na-22 positron emission isotope are spaced by 2 mm, and the graph in FIG. 9 shows positron emissions detected by a pair of z-detector units.

Figure 10:
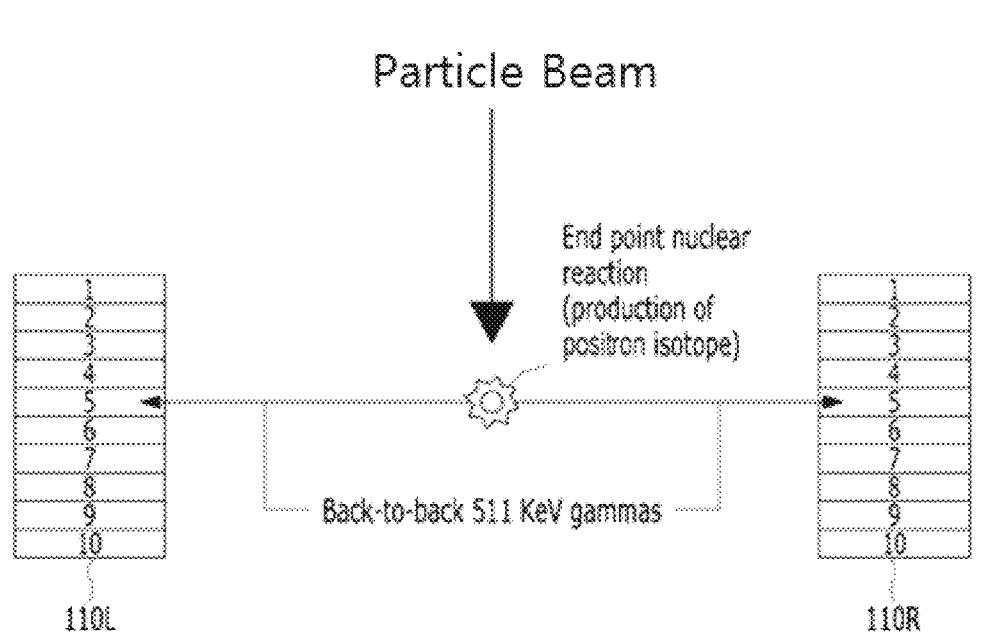
FIG. 10 is a front view of a pair of scintillator stacks.
Figure 11:
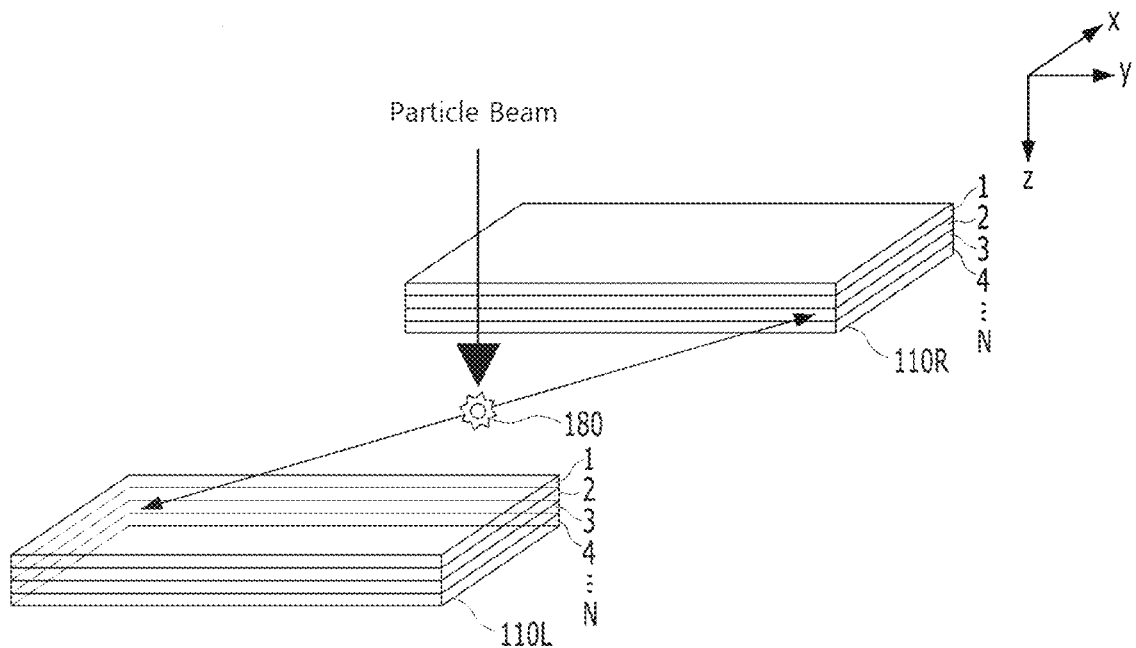
FIG. 11 is a perspective view of a pair of scintillator stacks in accordance with one exemplary embodiment of the present disclosure.

FIG. 10 is a front view of a pair of scintillator stacks, and FIG. 11 is a perspective view of a pair of scintillator stacks in accordance with one exemplary embodiment of the present disclosure.

Referring to FIGS. 10 and 11, an organism having tissues or a test subject (not shown) for treatment is positioned at a target position between stacks of scintillators 110L, 110R. In one embodiment, one pair or more pairs of scintillator stacks may be arranged on opposite sides of the target position in the planar dimension (e.g., x-y plane) defined by the length and width of the scintillators 100L-n, 100R-n.

Each sheet of the scintillators 110L, 110R may include a scintillation material capable of reacting to the production of the back-to-back gammas from the end point of the nuclear reaction after a proton beam is emitted to the target position in the organism or the test subject. Each pair in these stacks (e.g., one in the left scintillator stack 110L and the other in the right scintillator stack 110R on the same z-plane perpendicular to the beam direction) may determine one Z-position of the origin of the positron emission, and the photosensors (not shown) connected to that particular pair of scintillators (e.g., the $5^{th}$ pair of scintillators shown in FIG. 10) may generate substantially coincident electrical pulses based on the reaction of the scintillators.

In one embodiment, it may be determined whether an event detected by the pair of scintillators and the corresponding photosensor connected to the pair is a true event (indicating the back-to-back gammas from the end point of the nuclear reaction of the emitted particle from the particle emitter) or a false event (resulting from any other reactions in the environment) based on determining whether the event is detected within a predetermined period of time by the one or more detection units on the opposite sides across the target position. In one embodiment, the predetermined period of time is, e.g., 2 ns. According to embodiments of the invention, logic circuitry 190 connecting two photosensors on opposite sides of the target position may be provided to generate a signal indicating a true detection or a false detection based on whether a detected event was detected within the predetermined period of time by the two detection units on the opposite sides of the target position.

Figure 12:
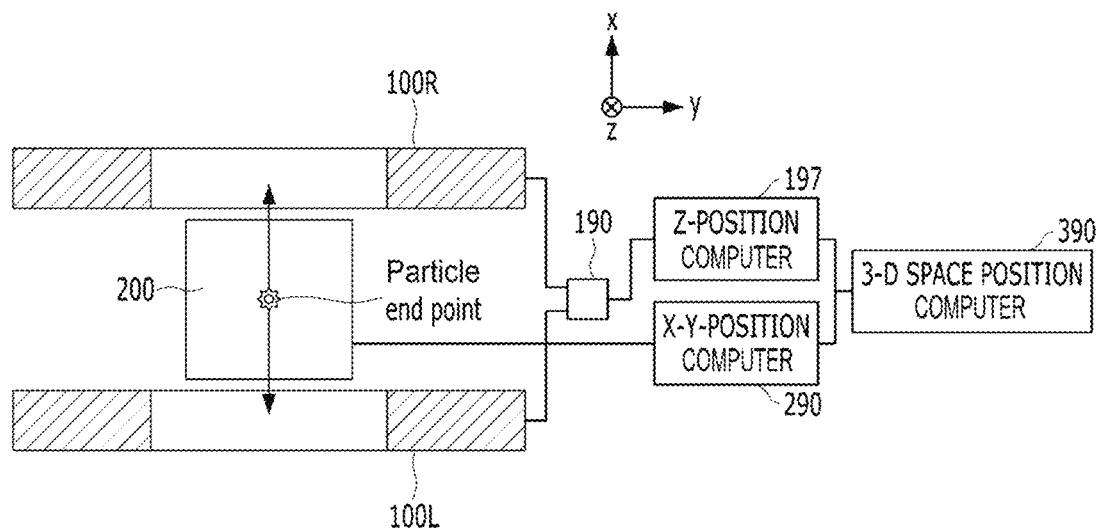
FIG. 12 is a top view of an arrangement of an x-y position detector used with the z-position detectors.
Figure 13:
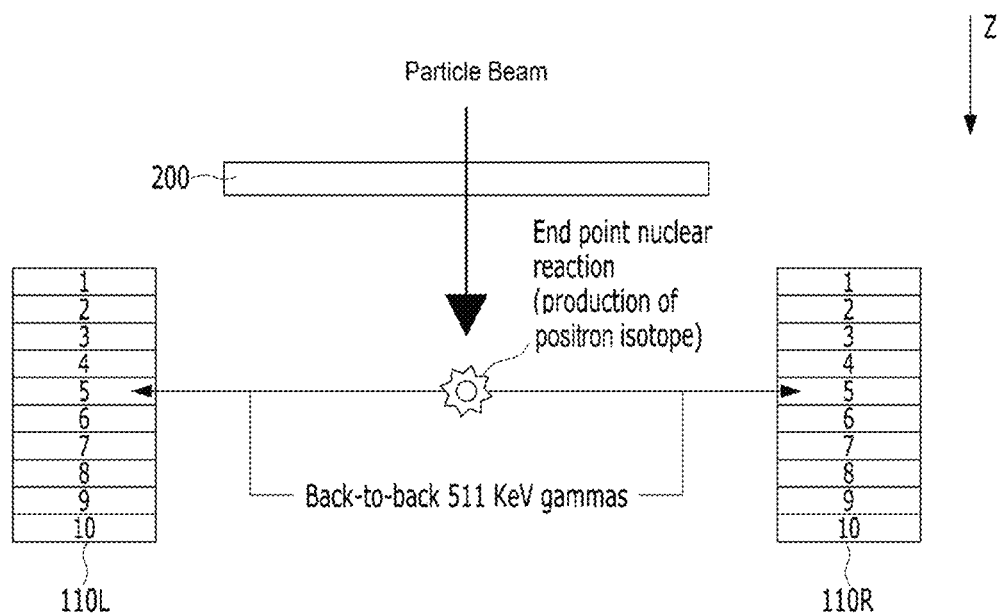
FIG. 13 is a front view of the arrangement in accordance with one exemplary embodiment of the present disclosure.

FIG. 12 is a top view of an arrangement of an x-y position detector used with the z-position detectors, and FIG. 13 is a front view of the arrangement in accordance with one exemplary embodiment of the present disclosure.

Referring to FIG. 12, an x-y position detector 200 (e.g. length/width plane) may be combined with stacks of z-position detectors 100L, 100R (e.g., height) to calculate the 3-dimensional position of the end-point nuclear reaction. In accordance with one embodiment, the x-y detector 200 may be positioned on the x-y plane perpendicular to the beam path defined by a particle beam, and the x-y detector 200 may detect the position at which the proton beam experiences the end-point nuclear reaction along the x-y plane. The x-y detector 200 may be any suitable two-dimensional beam detector, for instance, using an electrode, an insulation layer, and a photoconduction layer in the pertinent art, such as in U.S. patent application Ser. Nos. 16/036,856 and 16/456,145, which are herein incorporated by reference in their entirety. By way of example, the x-y detector 200 may be arranged between the charged particle beam emitter and a patient, such that the particle beam is irradiated against the patient after passing through the x-y detector.

Further, the z position computing circuit 197 may determine the position of the end-point nuclear reaction along the z plane based on the information from z-detector stacks 100L, 100R and the logic circuit 190. In one example, the z position computing circuit 197 may determine the position of the end-point nuclear reaction as the z position of the particular detection unit 100-n that produced a True signal (i.e., as a result of coincidence of back-to-back gammas). In addition, the combined outputs of the x-y position computing circuit 290 and the z position computing circuit 197 may enable the computing circuitry 390 to identify the three-dimensional position of the end-point nuclear reaction in all of the x-y- and z-planes. In one embodiment, the z position computing circuit 197, the x-y position computing circuit 290, and the computing circuitry 390 may include a hardware processor and memory, with software/firmware installed thereon, capable of computing dimensional positions. Further, these computing circuits may be integrated into one semiconductor chip or one computer, although they are depicted in separate blocks in FIG. 12.

Figure 14:
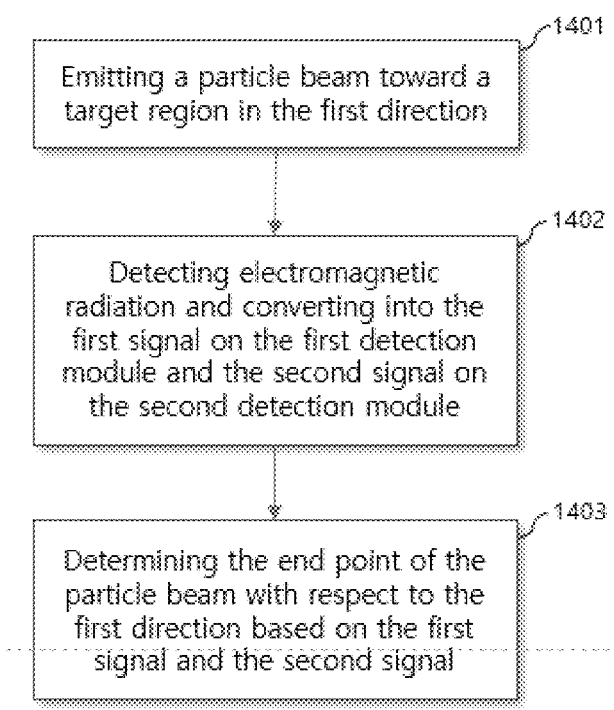
FIG. 14 is a flowchart of a method for operating a Bragg peak detection system according to one embodiment.

FIG. 14 is a flowchart of a method for operating a Bragg peak detection system according to one embodiment of the present disclosure. The Bragg peak detection system may include a proton or carbon ion beam to emit protons or carbon ions to the target point of a patient, a pair of detection modules each including a stack of scintillators and photosensors, and a coincidence detection circuit to determine whether an end-point nuclear reaction is a true or false event. The method may be performed and operated electronically using a Graphical User Interface (GUI) in a computer system. For example, a user may interact with a GUI of a computer system to generate commands to control the Bragg peak detection system to emit protons or carbon ions and detect a nuclear reaction at the end point. The computer system may then convert the received signals into an image to be displayed on a display device or stored in computer storage (e.g., memory).

In one embodiment, the two or more paired detection elements are arranged in stacks, with one detection element of each pair in a separate stack, and the one or more computers detect the position of the end point of the nuclear reaction in the height direction, parallel to the height of the stacks. In one embodiment, the one or more computers include processing circuitry and memory, and embodiments further include display devices to display the position of the end point of the nuclear reaction in a visual format.

That is, a method of real-time Bragg peak detection may be based on a detection system including two or more paired detection elements on opposite side of a target region, logic circuitry connecting each detection elements of the respective pairs, a beam emitter to emit a charged particle beam to have the end point of a nuclear reaction within the target region, and one or more computers to control the beam emitter and to determine, based on the output from the logic circuitry, whether a detected signal corresponds to a true event (or in other words, the generation of the back-to-back gammas in the end point of a nuclear reaction within the target region based on annihilation of a positron) or a false event based on any other reaction or environmental noise.

Further, an exemplary embodiment of a method in which the real-time in vivo Bragg peak detection system as shown in FIGS. 4-7B and 12-13 may be employed for acquiring an end position of a particle beam will now be described with respect to the following flow diagram of the method depicted in FIG. 14. It should be apparent to those of ordinary skill in the art that the figure represents a generalized illustration and that other steps may be added, or existing steps may be removed, modified or rearranged without departing from the scope of the present invention. In addition, the method is described with respect to the Bragg peak detection system as shown in FIGS. 4-7B and 12-13 by way of example and not limitation, and the method may be performed in other types of Bragg peak systems.

At step 1401, a particle beam (e.g., a beam of protons or carbon ions) is emitted from an emitter toward a target point of a patient or a test subject in the first direction, such that the annihilation of positron renders emission of electromagnetic radiation (e.g., back-to-back gammas).

At step 1402, the electromagnetic radiation (e.g., one of the back-to-back gammas) is detected by one sheet of scintillator among the stacks of first detection module and converted into the first pulse by one photosensor connected to the scintillator sheet of the first detection module. Substantially simultaneously, the electromagnetic radiation (e.g., the other of the back-to-back gammas) is detected by one sheet of scintillator among the stacks of second detection module and converted into the second pulse by one photosensor connected to the scintillator sheet of the second detection module.

At step 1403, a coincidence detection circuit determines whether the first pulse and the second pulse took place within a certain time window (e.g., 2 ns, 2.5 ns, etc.) and concludes that the electromagnetic radiation is a true or false event. In the case of a true event, the position of the particular pair of scintillators that detected the gammas is determined as the end point of the particle beam in the first direction (e.g., z-direction) by the computer. Further, the end point in the second and third directions can be determined using an x-y detector, and thus the three-dimensional coordinate of the end point can be detected.

A Bragg peak detector according to one or more embodiments of the present disclosure can be used to determine the end point of the particle beam in patient during a particle therapy, using the high decay rate of the shorter half life isotopes, such as $^{10}C$ and $^{15}O$. This detector can be operated at a high background environment of the treatment room during the on time of the particle beam.

A Bragg peak detector according to one or more embodiments of the present disclosure can be used for the real time determination of the Bragg peak of the particle therapeutic beam in vivo, in real time, and operable in a high radiation background environment.

Using this detector, the planar geometry of a stack of z-detection elements can determine the z-position of the end point, and no precision light travel time differences is required. Also, a time logic circuit is used between each pair of coplanar detection unit. A true signal is produced when the timing of the pair is "coincident" (e.g. within 2 nanoseconds).

This detector can be used in conjunction with a two-dimensional x-y detector intercepting the particle beam placed in front of the patient. The z-position determined from this detector together with the x-y information can uniquely determinate the three-dimensional position of the end-point of the particle beam.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

What is claimed is:

1. A real-time detector of radiation emission, comprising:
an emitter configured to emit a particle beam toward a target region in a first direction, thereby creating emission of electromagnetic radiation in the target region;
a first detection module comprising a stack of first scintillators and first photosensors respectively connected to the first scintillators and configured to detect the electromagnetic radiation and convert into a first signal, the first scintillators and first photosensors being stacked in the first direction;
a second detection module comprising a stack of second scintillators and second photosensors respectively connected to the second scintillators and configured to detect the electromagnetic radiation and convert into a second signal, the second scintillators and second photosensors being stacked in the first direction; and
circuitry configured to determine an end point of the particle beam with respect to the first direction based on the first signal and the second signal,
wherein the circuitry is further configured to in response to detecting that the first signal and the second signal are generated respectively from a first scintillator and photosensor and a second scintillator and photosensor disposed commonly on the same plane perpendicular to the first direction, determine that the first signal and the second signal coincide.

2. The detector of claim 1, wherein each first scintillator and photosensor of the first detection module and each corresponding second scintillator and photosensor of the second detection module are disposed commonly along a plane perpendicular to the first direction.

3. The detector of claim 1, wherein the first detection module and the second detection module are disposed on opposite sides across the target region.

4. The detector of claim 1, wherein the coincidence detection circuit comprises a comparator to determine whether the first signal and the second signal coincide.

5. The detector of claim 4, wherein the comparator is configured to, in response to detecting that the first signal and the second signal are within a predetermined time window, determine that the first signal and the second signal coincide.

6. The detector of claim 1, wherein the first and second scintillators are in the form of a sheet, a plate, a strip, or any other flat-shaped material.

7. The detector of claim 1, wherein the first and second scintillators are selected from at least one of a plastic scintillator, LYSO, YSO, BGO, and NaI.

8. The detector of claim 1, wherein the first and second photosensors are a photomultiplier tube (PMT) or a solid state photodetector, and
wherein each of the first and second scintillators is connected to one or more photosensors.

9. The detector of claim 1, further comprising a planar detector disposed perpendicular to the first direction and configured to determine the end point of the particle beam with respect to second and third directions perpendicular to the first direction.

10. The detector of claim 1, wherein the particle beam is a proton beam or a heavy ion beam.

11. The detector of claim 1, wherein the circuitry is configured to determine the end point of the particle beam in real-time while the particle beam is being emitted.

12. A method of detecting radiation emission in vivo and in real-time, comprising:
emitting a particle beam toward a target region in a first direction, thereby creating emission of electromagnetic radiation in the target region;
detecting the electromagnetic radiation and converting into a first signal on a first detection module comprising a stack of first scintillators and first photosensors respectively connected to the first scintillators, the first scintillators and first photosensors being stacked in the first direction;
detecting the electromagnetic radiation and converting into a second signal on a second detection module comprising a stack of second scintillators and second photosensors respectively connected to the second scintillators, the second scintillators and second photosensors being stacked in the first direction; and
determining an end point of the particle beam with respect to the first direction based on the first signal and the second signal,
wherein the determining comprises determining that the first signal and the second signal coincide, in response to detecting that the first signal and the second signal are generated respectively from a first scintillator and photosensor and a second scintillator and photosensor disposed commonly on the same plane perpendicular to the first direction.

13. The method of claim 12, wherein each first scintillator and photosensor of the first detection module and each corresponding second scintillator and photosensor of the second detection module are disposed commonly along a plane perpendicular to the first direction.

14. The method of claim 12, wherein the first detection module and the second detection module are disposed on opposite sides across the target region.

15. The method of claim 12, wherein the determining of the end point comprises comparing the first signal with the second signal to determine whether the first signal and the second signal are within a predetermined time window.

16. The method of claim 12, wherein the first and second scintillators are in the form of a sheet, a plate, or any other flat-shaped material.

17. The method of claim 12, wherein the first and second scintillators are selected from at least one of a plastic scintillator, LYSO, YSO, BGO, and NaI.

18. The method of claim 12, wherein the first and second photosensors are a photomultiplier tube (PMT) or a solid state photodetector, and
wherein each of the first and second scintillators is connected to one or more photosensors.

19. The method of claim 12, further comprising determining the end point of the particle beam with respect to second and third directions perpendicular to the first direction based on a planar detector disposed perpendicular to the first direction.

20. The method of claim 12, wherein the determining further comprises determining the end point of the particle beam in real-time while the particle beam is being emitted.

* * * * *